(12) United States Patent
Smith et al.

(10) Patent No.: US 11,292,924 B2
(45) Date of Patent: Apr. 5, 2022

(54) THERMAL CHEMICAL VAPOR DEPOSITION COATED ARTICLE AND PROCESS

(71) Applicant: SILCOTEK CORP., Bellefonte, PA (US)

(72) Inventors: David A. Smith, Bellefonte, PA (US); Min Yuan, State College, PA (US); James B. Mattzela, Port Matilda, PA (US); Paul H. Silvis, Port Matilda, PA (US)

(73) Assignee: Silcotek Corp., Bellefonte, PA (US)

( * ) Notice: Subject to any disclaimer, the term of this patent is extended or adjusted under 35 U.S.C. 154(b) by 1394 days.

(21) Appl. No.: 14/680,669

(22) Filed: Apr. 7, 2015

(65) Prior Publication Data

US 2015/0283307 A1    Oct. 8, 2015

Related U.S. Application Data (60) Provisional application No. 61/976,789, filed on Apr. 8, 2014.

(51) Int. Cl.
*C09D 5/16*    (2006.01)
*C23C 16/44*    (2006.01)
(Continued)

(52) U.S. Cl.
CPC ............. *C09D 5/1625* (2013.01); *C09D 5/16* (2013.01); *C23C 16/0227* (2013.01);
(Continued)

(58) Field of Classification Search
CPC ........ C09D 5/1625; C09D 5/16; C23C 16/56; C23C 16/0227; C23C 16/30; C23C 16/44;
(Continued)

(56) References Cited

U.S. PATENT DOCUMENTS

| | | | |
|---|---|---|---|
| 4,579,752 A | 4/1986 | Dubois et al. | |
| 4,671,997 A | 6/1987 | Galasso et al. | |

(Continued)

FOREIGN PATENT DOCUMENTS

| | | | |
|---|---|---|---|
| EP | 1150345 A2 | 10/2001 | |
| EP | 1988190 A2 | 11/2008 | |

(Continued)

OTHER PUBLICATIONS

Sigma Aldrich (Sigma Aldrich, "Syringe needle gauge chart," p. 1-3, http://www.sigmaaldrich.com/chemistry/stockroom-reagents/learning-center/technical-library/needle-gauge-chart.html, published Mar. 20, 2014, accessed Jul. 16, 2017).*

(Continued)

*Primary Examiner* — James C Yager
(74) *Attorney, Agent, or Firm* — Saxton & Stump, LLC (57) ABSTRACT

A coated article is disclosed. The article includes a coating formed by thermal decomposition, oxidation then functionalization. The article is configured for a marine environment, the marine environment including fouling features. The coating is resistant to the fouling features. Additionally or alternatively, the article is a medical device configured for a protein-containing environment, the protein-containing environment including protein adsorption features. The coating is resistant to the protein adsorption features.

18 Claims, 4 Drawing Sheets

(51) Int. Cl.
  *C23C 16/56* (2006.01)
  *C23C 16/02* (2006.01)
  *C23C 16/30* (2006.01)

(52) U.S. Cl.
  CPC .............. *C23C 16/30* (2013.01); *C23C 16/44* (2013.01); *C23C 16/56* (2013.01); *A61L 2420/02* (2013.01); *Y10T 428/13* (2015.01); *Y10T 428/263* (2015.01); *Y10T 428/31612* (2015.04); *Y10T 428/31663* (2015.04)

(58) Field of Classification Search
  CPC ..... Y10T 428/31663; Y10T 428/31612; Y10T 428/263; Y10T 428/13; A61L 2420/02
  USPC .............. 428/34.1, 334, 429, 447; 427/2.24; 556/487
  See application file for complete search history.

(56) References Cited

U.S. PATENT DOCUMENTS

| | | | |
|---|---|---|---|
| 4,713,661 A | 12/1987 | Boone et al. | |
| 4,714,632 A | 12/1987 | Cabrera et al. | |
| 4,741,964 A | 5/1988 | Haller | |
| 4,749,631 A | 6/1988 | Haluska et al. | |
| 4,753,856 A | 6/1988 | Haluska et al. | |
| 4,792,460 A | 12/1988 | Chu et al. | |
| 4,842,888 A | 6/1989 | Haluska et al. | |
| 5,160,544 A | 11/1992 | Garg et al. | |
| 5,249,554 A | 10/1993 | Tamor et al. | |
| 5,250,451 A | 10/1993 | Chouan | |
| 5,270,082 A | 12/1993 | Lin et al. | |
| 5,299,731 A | 4/1994 | Liyanage et al. | |
| 5,480,677 A | 1/1996 | Li et al. | |
| 5,481,135 A | 1/1996 | Chandra et al. | |
| 5,562,952 A | 10/1996 | Nakahigashi et al. | |
| 5,563,102 A | 10/1996 | Michael | |
| 5,818,071 A | 10/1998 | Loboda et al. | |
| 5,825,078 A | 10/1998 | Michael | |
| 6,159,871 A | 12/2000 | Loboda et al. | |
| 6,444,326 B1 | 9/2002 | Smith | |
| 6,472,076 B1 | 10/2002 | Hacker | |
| 6,511,760 B1 | 1/2003 | Barone et al. | |
| 6,531,398 B1 | 3/2003 | Gaillard et al. | |
| 6,593,655 B1 | 7/2003 | Loboda et al. | |
| 7,070,833 B2 | 7/2006 | Smith et al. | |
| 7,867,627 B2 | 1/2011 | Smith et al. | |
| 2003/0138645 A1* | 7/2003 | Gleason .................... | B05D 1/60 428/447 |
| 2003/0186000 A1 | 10/2003 | Li et al. | |
| 2003/0219562 A1* | 11/2003 | Rypacek ................ | A61L 31/10 428/36.91 |
| 2004/0175579 A1 | 9/2004 | Smith et al. | |
| 2005/0271893 A1 | 12/2005 | Kobrin et al. | |
| 2006/0216952 A1 | 9/2006 | Bhanap et al. | |
| 2006/0228966 A1* | 10/2006 | Gleason .................... | A61L 15/24 442/123 |
| 2007/0189917 A1* | 8/2007 | Stinson ................. | A61L 31/022 420/468 |
| 2008/0254304 A1* | 10/2008 | Sakhrani ................ | B05D 3/145 428/447 |
| 2009/0230558 A1 | 9/2009 | Matsuoka | |
| 2012/0251797 A1 | 10/2012 | Smith et al. | |
| 2013/0211344 A1* | 8/2013 | Rodriguez .......... | A61M 5/3129 604/230 |
| 2013/0244025 A1 | 9/2013 | Smith et al. | |
| 2014/0370300 A1 | 12/2014 | Smith | |
| 2015/0030885 A1 | 1/2015 | Smith | |
| 2015/0283307 A1 | 1/2015 | Smith et al. | |

FOREIGN PATENT DOCUMENTS

| | | | |
|---|---|---|---|
| WO | 2009032488 A1 | 3/2009 | |
| WO | 2009143618 A1 | 12/2009 | |
| WO | WO 2012047945 A2 * | 4/2012 | ......... C23C 16/0272 |

OTHER PUBLICATIONS

Ruiter (Ruiter, Mathew, "French, gauge, OD/ID, mm, inches, what does it all mean?," 2011, p. 1-5, https://www.alnmag.com/article/2011/08/french-gauge-odid-mm-inches-what-does-it-all-mean).*
Dict (Dict, "Surface," The Collaborative International Dictionary of English, Also referred to as GCIDE: Webster's Revised Unabridged Dictionary, 1913, C. & G. Merriam Co., Springfield, Mass. Under the direction of Noah Porter, D.D., LL.D., p. 1-4).*
Vasin A V et al: "Light-emitting properties of amorphous Si:C:O:H layers fabricated by oxidation of carbon-rich a-Si:C:H films", Solid State Sciences, Elsevier, Paris, FR, vol. 11, No. 10, Oct. 1, 2009 (Oct. 1, 2009), pp. 1833-1837, XP026653063, ISSN: 1293-2558, DOI:DOI:10,1016/J.SOLIDSTATESCIENCES. May 30, 2009.
Narita et al: "Interpretation of initial stage of 3C-SiC growth on Si(100) using dimethylsilane", Applied Surface Science, Elsevier, Amsterdam, NL, vol. 252, No. 10, Mar. 15, 2006 (Mar. 15, 2006), pp. 3460-3465, XP005294988, ISSN: 0169-4332, COI:DOI:10.1016/J.APSUSC.2005.05.021.
Shinohara M et al: "infrared study of carbon incorporation during chemical vapor deposition of SiC using methylsilanes", Applied Surface Science Elsevier Netherlands, vol. 175-176, May 15, 2001 (May 15, 2001), pp. 591-596, XP002620548, ISSN: 0169-4332.
H.E. O'neal and M.A. Ring, "Mechanism of the Thermal Decomposition of Dimethylsilane at Atmostpheric Pressures in the Gas Phase", Organometallics, American Chemical Society, vol. 7, No. 5, May 1988, pp. 1017-1025.
Restek Performance Coatings Service Through Technology, www.restekcorp.com, 2003, 1 pg.
D.A. Smith, D. Shelow and G. Barone, "Instrument and Sampling Equipment Passivation Requirements to Meet Current Demands for Low-Level Sulfur Analysis," 2001, 37 pgs.
Fast Facts At-a-Glance Product Information from Restek, Silcosteel-UHV, Dramatically Reduce Outgassing in UHV Systems, www.restekcorp.com, 2001, 2 pgs.
Fast Facts At-a-Glance Product Information from Restek, Silcosteel-CR, Achieve Specialty Alloy Performance Using Austenitic Stainless Steels, www.restekcorp.com, 2004, 4 pgs.
D.A. Smith, G.B. Stidsen, B. Burger and D. Shelow, "The Containment and Transfer of Trace Sulfur Gases at Low-PPBV Levels," 2001, 37 pgs.
G.A. Barone, D.A. Smith and M. Higgins, "Anti-Corrosive and Anti-Coking Properties of Unique Surface Coatings for Metal Substrates in Petrochemical Service," www.restekcorp.com, obtained Feb. 2015, 19 pgs.
G.A. Barone, D.A. Smith and D. Shelow, "Advantages to Using Inert, Coated Components for Sampling & Measurement of Organo-Sulfur Compounds," www.restekcorp.com, obtained Feb. 2015, 17 pgs.
R.L. Firor and B.D. Quimby, "Dual-Channel Gas Chromatographic System for the Determination of Low-Level Sulfur in Hydrocarbon Gases," Agilent Technologies, Inc., Mar. 2003, 10 pgs.
R.L. Firor, "Use of GC/MSD for Determination of Volatile Sulfur: Application in Natural Gas Fuel Cell Systems and Other Gaseous Streams," Agilent Technologies, Inc., Nov. 2001, 10 pgs.
V. Pretorius and J.D. Du Toit, "Gas Chromatography in Glass and Fused Silica Capillary Columns: Deactivation of the Inner Surface Using Silicon Films," Journal of HRC & CC, 1981, 2 pgs.
D.A. Smith, M. Higgins and G. Barone, "Evaluation of System Surfaces in Low-Level Sulfur Analysis for the Petrochemical Industry," www.restekcorp.com, obtained Feb. 2015, 37 pgs.
G. Barone, D.Smith and M. Higgins, "Selection of Surface Coatings for Process Lines and Equipment Used in Corrosive and Reactive Streams", Analytical Solutions for Energy Optimization & Environmental Compliance, The 54th Annual Symposium of the Analysis Division, Apr. 2009, 17 pgs.
J. De Zeeuw, G. Barone and M. Higgins, "Comparing Surface Adsorption Effects During the Analysis of Mercury and Sulfur Containing Streams," www.restekcoatings.com, obtained Feb. 2015, 30 pgs.
G. Barone, D. Smith, M. Higgins and T. Neeme, "Study of Chemical and Physical Adsorption Properties of Moisture, Sulfur, and Mer- (56) References Cited

OTHER PUBLICATIONS cury Streams Through a Variety of Tubing Substrates," ISA 53rd Analysis Division Symposium, 2008, 9 pgs.
D.A. Smith and J.B. Mattzela, The Deposition and Functionalization of Silicon-Based Materials to Prevent Surface Corrosion, Adsorption, Contamination and Catalytic Interactions, MS&T'09, Oct. 2009, 21 pgs.
W. Bertsch and V. Pretorius, "Deactivation of Metal Surfaces for Capillary Columns for GC by Deposition of Silicon," Journal of HRC&CC, 1982, 3 pgs.
G.G. Gerhab and A. Schuyler, "Highly Inert Sample Pathways," 1996, 16 pgs.
A. Schuyler, J.W. Stauffer, C.E. Loope and C.R. Vargo, "Highly Efficient and Inert Stainless Steel GC Columns: A Durable, Flexible Alternative to Fused Silica," Elsevier Science Publishers, 1992, 6 pgs.
G. Gerhab and A. Schuyler, "Efficient and Rapid GC Analysis With Rugged Metal Microbore Capillary Columns," www.restekcorp.com, obtained Feb. 2015, 18 pgs.
J. De Zeeuw, "Deactivation of Metal Surfaces: Applications in Gas Chromatography (GC) for the Past 15 Years," American Laboratory, Nov. 2012, 10 pgs.

\* cited by examiner

FIG. 7

THERMAL CHEMICAL VAPOR DEPOSITION COATED ARTICLE AND PROCESS

PRIORITY

This application is a non-provisional patent application claiming priority and benefit of U.S. Provisional Patent Application No. 61/976,789, entitled "COATED ARTICLE", the entirety of which is hereby incorporated by reference.

FIELD

The present disclosure is directed to coated articles and coating processes. More particularly, the disclosure is directed to articles coated with thermal chemical vapor deposition coatings.

BACKGROUND

Often, surfaces of substrates do not include desired performance characteristics. The failure to include specific desired performance characteristics can result in surface degradation in certain environments, an inability to meet certain performance requirements, or combinations thereof. Biofouling and/or biocontamination presents a severe challenge in a wide range of applications from biomedical devices and protective apparel in hospitals, medical implants, biosensors, food packaging and storage, water purification systems, to marine and industrial equipment. For example, in marine applications, biofoulants, such as, algae, barnacles, tunicates, and mussels frequently invade ship hulls, piers, offshore oil and gas platforms. Such biofoulants cause increased drag and damage of materials, which results in billion dollars of cost due to decreased fuel efficiency.

Another problem, known as protein adsorption exists in the human body, affecting contact lenses, endotracheal tubes, artificial joints, biomedical implants, and other similar devices. Protein adsorption involves protein sticking to surfaces of biomedical devices. This causes millions of contact lens infections every year and requires heart patients to take anti-clotting drugs. Adsorption of proteins to biological sampling systems also reduces sensitivity in the case of in vitro diagnostics.

In general, an inert surface resistant to biofouling is needed. However, existing solutions to biofouling have significant drawbacks. For example, the most commonly used substances to impart protein resistance to a surface are based on oligo(ethylene glycol) or poly(ethylene glycol) (PEG). However, such substances are not stable and have a tendency to auto-oxidize in the presence of oxygen, thereby losing protein-resistance.

In marine applications, current anti-fouling strategies utilize paints or coatings having heavy metals that gradually dissolve and release toxic substances like copper, tin, zinc or organic biocides. Such toxic substances poison everything and anything that attaches to a ship hull. The environmental concerns have prompted the international maritime community to ban tin-based marine coatings on newly built vessels, and United States Navy standards require that replacement coatings be environmentally benign and stable for ten to twelve years.

Accordingly, a coated article that does not suffer from one or more of the above drawbacks would be desired in the art.

SUMMARY

According to an embodiment of the present disclosure, an article includes a coating formed by oxidation then functionalization. The article is configured for a marine environment, the marine environment including fouling features. The coating is resistant to the fouling features.

According to an embodiment of the present disclosure, a thermal chemical vapor coated article includes a coating formed by thermal decomposition on a stainless steel surface, oxidation then functionalization. The article is a medical device configured for a protein-containing environment, the protein-containing environment including protein adsorption conditions. The coating is resistant to the protein adsorption conditions. The thermal decomposition is by introduction of dimethylsilane. The oxidation is by introduction of zero air. The functionalization is by introduction of trimethylsilane. The medical device is a biomedical device, surgical equipment, a portion of a medical diagnostic sampling system, a medical implant, or a combination thereof.

Further aspects of embodiments of the invention are disclosed herein. The features as discussed above, as well as other features and advantages of the present application, will be appreciated and understood by those skilled in the art from the following drawings and detailed description.

BRIEF DESCRIPTION OF THE DRAWINGS

Wherever possible, the same reference numbers will be used throughout the drawings to represent the same parts.

DETAILED DESCRIPTION OF EXEMPLARY EMBODIMENTS

U.S. patent application Ser. No. 13/504,533, filed Apr. 27, 2012, and titled "Coating, Coated Article, and Method of Applying a Coating," is hereby incorporated by reference in its entirety. Provided is a coating, a coated article, and a chemical vapor deposition process for producing a coated article. Embodiments of the present disclosure permit coatings, for example, in comparison to similar coatings failing to include one or more of the features disclosed herein, to include additional properties relating to having protein resistance and general anti-biofouling properties, having consistent or substantially consistent thickness within tube or tube-like articles, being devoid or substantially devoid of build up in entrances of the tube or tube-like articles, or a combination thereof.

In one embodiment, a coating 101 (see FIG. 1) is resistant to fouling conditions. As used herein, "fouling conditions" refer to conditions that are present in the presence of micro-organisms, such as, alga, barnacles, tunicates, and mussels that frequently invade ship hulls, piers, offshore oil and gas platforms. In further embodiments, the coating is more resistant to such conditions than uncoated alloys, teflon, stainless steel, or a combination thereof.

In one embodiment, the coating 101 is resistant to protein adsorption conditions. As used herein, "protein adsorption conditions" refer to conditions with protein at a concentration that is capable of adsorption to a stainless steel surface.

Figure 1:
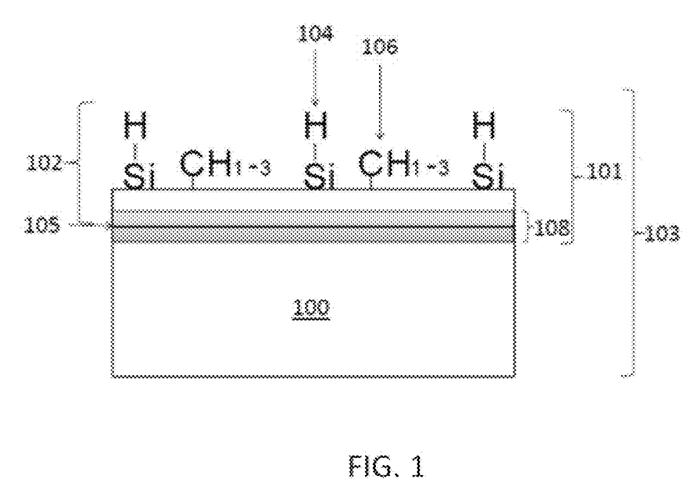
FIG. 1 shows a schematic view of an article having a coating with a layer formed from decomposition of a material according to an embodiment of the disclosure.

A coating process 200 (see FIG. 2) forms the coating 101 on a substrate 100 of an article 103, for example, as is shown in FIG. 1. The article 103 is any suitable object that benefits from anti-fouling properties but is capable of withstanding processing temperatures of the coating process 200. Suitable objects include, but are not limited to, biomedical devices, surgical equipment, medical diagnostic sampling systems, medical implants, parts of marine and/or industrial equipment, coastal marine structures, offshore structures, ocean/island vessels, similar objects, or combinations thereof.

For example, in one embodiment, the article 103 is a coronary stent (a small metal mesh tube that acts as a scaffold to provide support inside the coronary artery). The coronary stent is created by any suitable technique, such as, within a coil, tubular mesh, or slotted tube framework. In a further embodiment, the coronary stent includes a strut pattern, strut width, a diameter (for example, between 2 and 6 mm), length (for example, between 8 mm and 50 mm), or a combination thereof. In one embodiment, the article 103 is a medical-grade probe, such as, a 316 stainless steel probe. The medical-grade probe has an internal diameter (for example, at or greater than 0.1 mm, between 1 mm and 3 mm, or any suitable combination, sub-combination, range, or sub-range thereof). The medical-grade probe is capable of use in a medical diagnostic system.

The article 103 includes a surface 105, which is or includes the interior surface, an exterior surface, or a combination thereof. The surface 105 has surface properties achieved through the coating process 200 controllably depositing a layer 102. The layer 102 imparts a surface effect to the substrate 100, the coating 101, the article 103, or combinations thereof. The substrate 100 is any suitable substrate, such as, a metallic substrate (ferrous or non-ferrous), stainless steel, titanium, a glass substrate, a ceramic substrate, ceramic matrix composite substrate, a composite metal substrate, a coated substrate, a fiber substrate, a foil substrate, a film, or a combination thereof.

Figure 2:
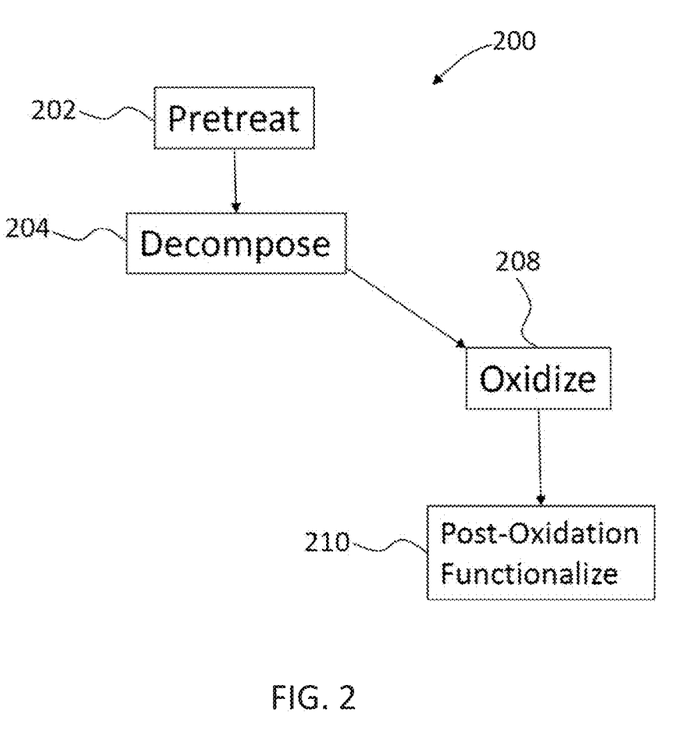
FIG. 2 shows a schematic view of a process according to an embodiment of the disclosure.

Referring to FIG. 2, the coating process 200 includes pretreatment (step 202), thermal decomposition (step 204), oxidation (step 208), post-oxidation functionalization (step 210), or a combination thereof. In one embodiment, the coating process 200 includes, consist of, or consists essentially of the pretreatment (step 202) and the thermal decomposition (step 204). In one embodiment, the coating process 200 includes, consist of, or consists essentially of the thermal decomposition (step 204), the oxidation (step 208), and the post-oxidation functionalization (step 210). In one embodiment, the coating process 200 includes, consist of, or consists essentially of the pretreatment (step 202), the thermal decomposition (step 204), the oxidation (step 208), and the post-oxidation functionalization (step 210).

The pretreatment (step 202) is or includes any suitable techniques taken to prepare a chamber, the surface 105, the substrate 100, or a combination thereof. In one embodiment, the chamber is a chemical vapor deposition chamber, for example, with tubing connections to allow gas flow in and out of the chemical vapor deposition chamber. In a further embodiment, the chamber includes multiple controlled inlets and outlets configured for providing and removing multiple gas streams and/or a vacuum connected to one or more outlet tubes.

Suitable techniques for the pretreatment (step 202) include, but are not limited to, cleaning, pre-heating, isolating the substrate 100 and/or the surface 105, surface treatment techniques, evacuating the chamber (for example, with the flow of gas and/or maintenance of a vacuum in the chamber providing a controlled atmosphere), flushing/purging the chamber (for example, with an inert gas such as nitrogen, helium, and/or argon), or a combination thereof. In one embodiment, a heat source controls the temperature in the chamber, for example, to desorb water and remove contaminants from the surface 105. In one embodiment, the heating is at a temperature above about 100° C. (for example, about 450° C.) and/or at a pressure (for example, between about 1 atmosphere and about 3 atmospheres, between about 1 atmosphere and about 2 atmospheres, between about 2 atmospheres and about 3 atmospheres, about 1 atmosphere, about 2 atmospheres, about 3 atmospheres, or any suitable combination, sub-combination, range, or sub-range therein). In one embodiment, the heating is for a period of time (for example, between about 3 minutes and about 15 hours, between about 0.5 hours and about 15 hours, for about 3 minutes, for about 0.5 hours, for about 2 hours, for about 15 hours, or any suitable combination, sub-combination, range, or sub-range therein).

In one embodiment, the pretreatment (step 202) includes pre-exposure of the substrate 100 to a thermal oxidative environment. Pre-exposure of the substrate 100 to the thermal oxidative environment pre-oxidizes the surface 105 of the substrate 100, increasing stability of both the surface 105 and the substrate 100. The increased stability of the substrate 100 increases the stability of the coating 101 formed over the substrate 100.

The thermal oxidative environment is at any suitable temperature(s) allowing oxidation. Suitable temperatures include, but are not limited to between about 100° C. and about 700° C., between about 100° C. and about 450° C., between about 100° C. and about 300° C., between about 200° C. and about 500° C., between about 300° C. and about 600° C., between about 450° C. and about 700° C., about 700° C., about 450° C., about 100° C., or any suitable combination, sub-combination, range, or sub-range thereof.

The substrate 100 is pre-exposed to the thermal oxidative environment for any suitable duration allowing oxidation. Suitable duration including, but are not limited to, between about 30 minutes and 6 hours, between about 30 minutes and about 4 hours, between about 1 hour and about 4 hours, up to about 10 hours, up to about 4 hours, up to about 2 hours, up to about 30 minutes, or any combination, sub-combination, range or sub-range thereof.

The increased stability of the coating 101 is detectable by contact angle measurements for both water and hexadecane, for example, after exposure of the substrate 100 to room air at 450° C. for 30 minutes. In one embodiment, the substrate 100 is X40CrMoV5-1 having a composition including by weight percent between about 0.37% and about 0.42% carbon, between about 0.90% and about 1.20% silicon, between about 0.30% and about 0.50% manganese, up to about 0.030% phosphorous, up to about 0.030% sulfur, between about 4.80% and about 5.50% chromium, between about 1.20% and about 1.50% molybdenum, between about 0.90% and about 1.10% vanadium, the rest being substantially iron.

In another embodiment, without pre-oxidation of the substrate 100, the contact angle of water on X40CrMoV5-1 after 30 minutes of exposure to 450° C. in room air drops to 28.8° from an initial value of 146.9°, a 118.1° change. However, with pre-oxidation of the substrate 100, the contact angle of water on X40CrMoV5-1 after 30 minutes of exposure to 450° C. in room air increases to 127.4° from an initial value of 126.2°, a 1.2° change. In another example, without pre-oxidation the contact angle of hexadecane on X40CrMoV5-1 after 30 minutes of exposure to 450° C. in room air drops to approximately 0° from an initial value of 92.3°, a 92.3° change. However, with pre-oxidation, the contact angle of hexadecane on X40CrMoV5-1 after 30 minutes of exposure to 450° C. in room air increases to 72.1° from an initial value of 66.5°, a 5.6° change.

The thermal decomposition (step 204) is or includes thermal decomposition of one or more precursor materials. In one embodiment, the precursor material is or includes dimethylsilane, for example, in gaseous form. In general, dimethylsilane is not readily obtainable due to the low demand for it. Dimethylsilane has been regarded as undesirable in some chemical vapor deposition applications because it includes carbon and is much more expensive than silane. Silane and the monomethyl analogue to dimethylsilane, methylsilane, are both pyrophoric and may explode in air. Dimethylsilane, although flammable, is not pyrophoric. Thus, use of dimethylsilane decreases safety risks. In addition, use of dimethylsilane results in inertness of a coating and/or chemical resistance, thereby protecting the surface 105 of the substrate 100. Other suitable precursor materials include, but are not limited to, trimethylsilane, dialkylsilyl dihydride, alkylsilyl trihydride, and combinations thereof. In one embodiment, the materials are non-pyrophoric, for example, dialkylsilyl dihydride and/or alkylsilyl trihydride.

The thermal decomposition (step 204) includes any suitable thermal decomposition parameters corresponding to the precursor material, for example, as is described in U.S. Pat. No. 6,444,326, which is incorporated herein by reference in its entirety, to apply material through deposition. If a thicker deposition of the layer 102 is desired, the deposition temperature, the deposition pressure, the deposition time, or a combination thereof are increased or decreased. Suitable thicknesses of the coating 101 include, but are not limited to, between about 100 nm and about 10,000 nm, between about 200 nm and about 5,000 nm, between about 300 nm and about 1,500 nm, or any suitable combination, sub-combination, range, or sub-range therein.

Additionally or alternatively, in one embodiment, a plurality of the layers 102 are applied by repeating the deposition. In one embodiment, the thermal decomposition (step 204) pressure is between about 0.01 psia and about 200 psia, 1.0 psia and about 100 psia, 5 psia and about 40 psia, about 1.0 psia, about 5 psia, about 40 psia, about 100 psia, 200 psia, or any suitable combination, sub-combination, range, or sub-range therein. In one embodiment, the thermal decomposition (step 204) temperature is between about 200° C. and 600° C., between about 300° C. and 600° C., between about 400° C. and about 500° C., about 300° C., about 400° C., about 500° C., about 600° C., or any suitable combination, sub-combination, range, or sub-range therein. In one embodiment, the thermal decomposition (step 204) period is for a duration of about 10 minutes to about 24 hours, about 30 minutes to about 24 hours, about 10 minutes, about 30 minutes, about 15 hours, about 24 hours, or any suitable combination, sub-combination, range, or sub-range therein.

The thermal decomposition (step 204) forms the layer 102, for example, having improved chemical resistance, improved inertness, and/or improved adhesion over non-diffusion coatings and/or coatings not having the thermally decomposed material. The layer 102 includes any suitable thermally decomposed material corresponding to the precursor material. The thermally decomposed material is formed by the thermal decomposition (step 204) at a pressure and a temperature sufficient to decompose the precursor material, thereby depositing constituents from the thermally decomposed material onto the substrate 100, for example, with an inert gas such as nitrogen, helium, and/or argon, as a partial pressure dilutant.

In one embodiment, the thermally decomposed material is or includes carbosilane (for example, amorphous carbosilane), corresponding to the precursor including the dimethylsilane, which, although not intending to be bound by theory, is believed to be a recombination of carbosilyl (disilyl or trisilyl fragments) formed from the carbosilane. In one embodiment, the thermally decomposed material includes molecules, such as, silicon, carbon, and hydrogen atoms, that serve as active sites. The molecules are positioned within the layer 102 and include a first portion 104 and a second portion 106. Generally, the first portion 104 and the second portion 106 of the layer 102 are not spatially resolvable (for example, the first portion 104 and the second portion 106 are defined by the molecules deposited on the layer 102 and the molecules are capable of being interspersed throughout the layer 102). Furthermore, use of the terms "first" and "second" is not intended to imply any sequentiality, difference in quantity, difference in size, or other distinction between the two portions. To the contrary, the terms "first" and "second" are used for distinguishing molecular composition of the two portions. For example, in one embodiment, as is shown in FIG. 1, the first portion 104 includes silicon and the second portion 106 includes carbon. In one embodiment, the first portion 104 and the second portion 106 are bound together randomly throughout the layer 102.

Figure 6:
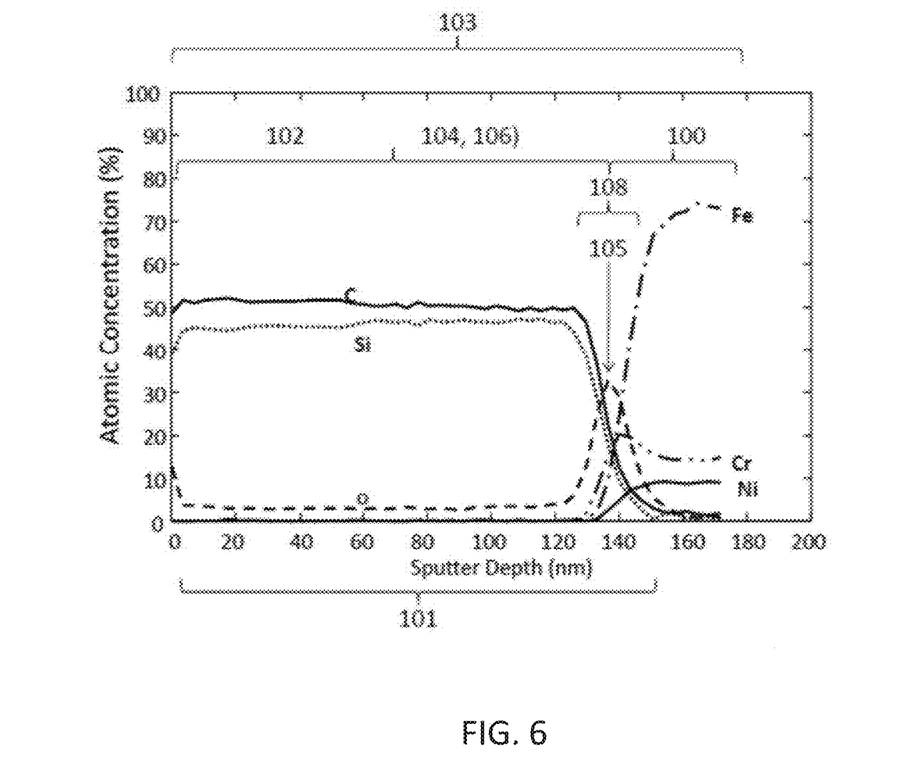
FIG. 6 shows an Auger Electron Spectroscopy plot of an article having a layer formed from decomposition of material according to an embodiment of the disclosure.

FIG. 6 shows the composition of an embodiment throughout the article 103 by Auger Electron Spectroscopy measurements according to an embodiment of the disclosure. FIG. 6 shows a diffusion region 108 within the article 103. It will be appreciated that precise measurement of the diffusion layer 108 via Auger Electron Spectroscopy can be offset by surface roughness of the substrate and coating and that the results shown are merely representative of one embodiment falling within the disclosure. Therefore, the diffusion region 108, as measured by Auger Electron Spectroscopy, is not an absolute measurement but a representation of the diffusion mechanism, according to the coating process 200.

In one embodiment, the composition of the layer 102 is about 1:0.95:0.12 ratio of C:Si:O. In contrast, the composition of the dimethylsilane introduced into the chemical vapor deposition chamber according to an embodiment has about a 2:1 ratio of C:Si. Although not intending to be bound by theory, it is believed that $CH_x$ (x=0-3) moieties are retained and Si—C bonds are broken thus indicating that layer 102 includes an amorphous array of Si—C bonding. The amorphous array provides additional benefits such as decreased cracking or flaking, for example, upon tensile or compressive forces acting on the substrate 100, increased adhesion, or a combination thereof. In one embodiment, multiple layers of the coating 101, or similar coatings, are deposited for thicker layers or for desired properties.

In one embodiment, upon the thermally decomposed materials forming the layer 102 through the thermal decomposition (step 204), the chamber is purged. The purging removes remaining decomposition materials, unbound thermally decomposed materials, and/or other materials or constituents present within the chamber.

The oxidation (step 208) is or includes exposure to any suitable chemical species or oxidation reagent capable of donating a reactive oxygen species under oxidation conditions to form the oxidized layer 107. The oxidation (step 208) is of the layer 102 and forms the oxidized layer 107. In an embodiment with the layer 102 being amorphous carbosilane, the oxidized layer 107 formed by the oxidation (step 208) is or includes amorphous carboxysilane. In general, the oxidation (step 208) are bulk reactions that affect the bulk of the coating 101. In one embodiment, the degree of oxidization is controlled by increasing or decreasing the temperature within the chamber, the exposure time within the chamber, the type and/or amount of diluent gases, pressure, and/or other suitable process conditions. Control of the degree of the oxidization increases or decreases the amount and/or depth of the oxidized layer 107 and, thus, the wear resistance and/or hardness of the coating 101.

Suitable oxidation reagents for the oxidation (step 208) include, but are not limited to, water (alone, with zero air, or with an inert gas), oxygen, air (alone, not alone, and/or as zero air), nitrous oxide, ozone, peroxide, or a combination thereof. As used herein, the term "zero air" refers to atmospheric air having less than about 0.1 ppm total hydrocarbons. In one embodiment, the oxidation reagent consists of gaseous reagents. Due to the gaseous processing agents (for example, dimethylsilane and/or nitrogen) being in the gas phase, use of the gaseous oxidation reagent results in simpler scale-up for manufacturing, a more transferable process, and a more economical process.

The oxidation reagent used for the oxidation (step 208) is introduced at any suitable operational conditions permitting the formation of the oxidized layer 107. Suitable operational conditions include, but are not limited to, being in the presence of an inert gas, being at a pressure (for example, between about 1 to 200 psia), being subjected to a temperature (for example, about 450° C.), being for a period of time (for example, for about two hours), other parameters as are described above with reference to the thermal decomposition (step 204), or a combination thereof.

In one embodiment, depending upon the selected species of the oxidation reagent, additional features are present, for example, for safety purposes. Such features include the chamber having a size, weight, and/or corrosion-resistance permitting reactions to occur safely. In one embodiment, to safely inject water into the chamber as the oxidation reagent, substantial cooling is used. For example, in embodiments with the chamber operating at temperature of greater than about 300° C., the chamber is first cooled below about 100° C., which is capable of resulting in a drain on energy and/or time of manufacturing resources.

Figure 3:
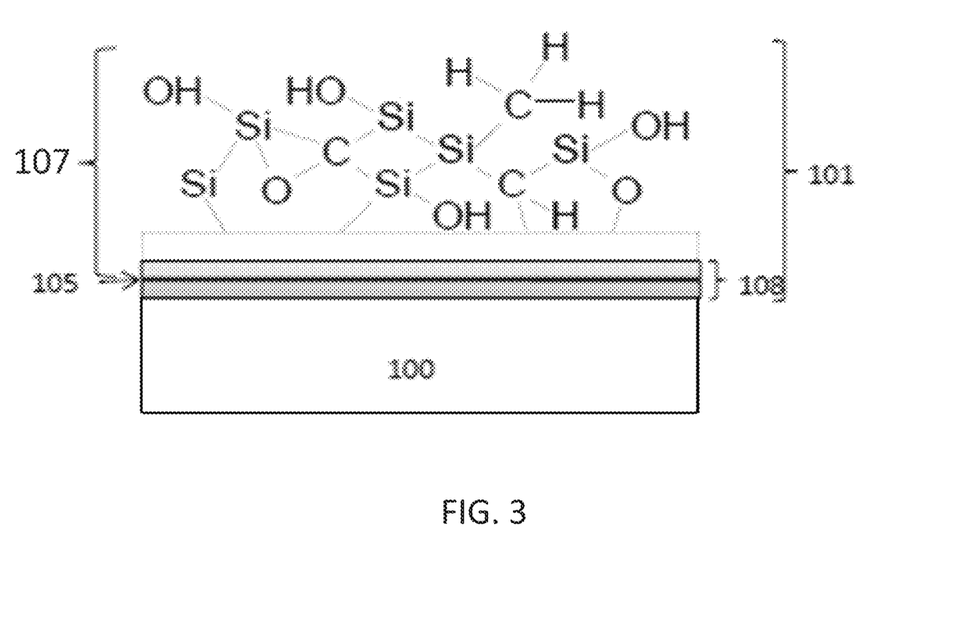
FIG. 3 shows a schematic view of an article having a coating with an oxidized layer formed according to an embodiment of the disclosure.

The oxidized layer 107 formed by the oxidation (step 208) includes properties corresponding to the oxidation reagent used and the operational parameters. In one embodiment, in comparison to the layer 102, the oxidized layer 107 is over-oxidized and/or has a contact angle on a Si wafer of about 60° has an increased amount of N—H, Si—OH, and/or C—OH groups, has fragile scratch resistance, has increased acid resistance, has increased corrosion resistance, or a combination thereof.

The oxidized layer 107 includes various comparative properties relative to the layer 102, and/or embodiments with the oxidized layer 107 being formed by different oxidation reagents. For example, the oxidized layer 107 has decreased chemical resistance, has decreased scratch resistance, has decreased hardness, or a combination thereof. In one embodiment, the oxidized layer 107 is oxidized and/or has a contact angle on a Si wafer of about 86.6° has decreased friction (for example, in comparison to embodiments with the oxidizing reagent being zero air and water), has decreased wear resistance (for example, in comparison to embodiments with the oxidizing reagent being zero air and water), includes Si—O—Si groups (for example, capable of being shown by FT-IR data having a growth of the Si—O—Si peak at 1026.9 cm$^{-1}$ compared to the non-water functionalized peak at 995.2 cm$^{-1}$), or a combination thereof. In one embodiment, the oxidized layer 107 is over-oxidized, has a decreased amount of C—H groups (for example, in comparison to embodiments with the oxidizing reagent being water alone), has a decreased amount of Si—C groups (for example, in comparison to embodiments with the oxidizing reagent being water alone), has an increased amount of Si—OH/C—OH groups (for example, in comparison to embodiments with the oxidizing reagent being water alone), or a combination thereof. In one embodiment, the oxidized layer 107 has lower coefficient of friction (for example, in comparison to embodiments with the oxidization agent being zero air and water), has increased wear resistance (for example, in comparison to embodiments with the oxidization agent being zero air and water), includes Si—O—Si groups, or a combination thereof.

In one embodiment, the coefficient of friction is decreased by the oxidation (step 208). For example, in an embodiment with the oxidation (step 208) of the layer 102, the layer 102 includes a first coefficient of friction (for example, about 0.97) prior to the oxidation (step 208) and a second coefficient of friction (for example, about 0.84) after the oxidation (step 208).

In one embodiment, the wear rate is decreased by the oxidation (step 208). For example, in an embodiment with the oxidation (step 208) of the layer 102, the layer 102 includes a first wear rate (for example, $4.73 \times 10^{-4}$ mm$^3$/N/m) prior to the oxidation (step 208) and a second wear rate (for example, about $6.75 \times 10^{-5}$ mm$^3$/N/m) after the oxidation (step 208).

Figure 7:
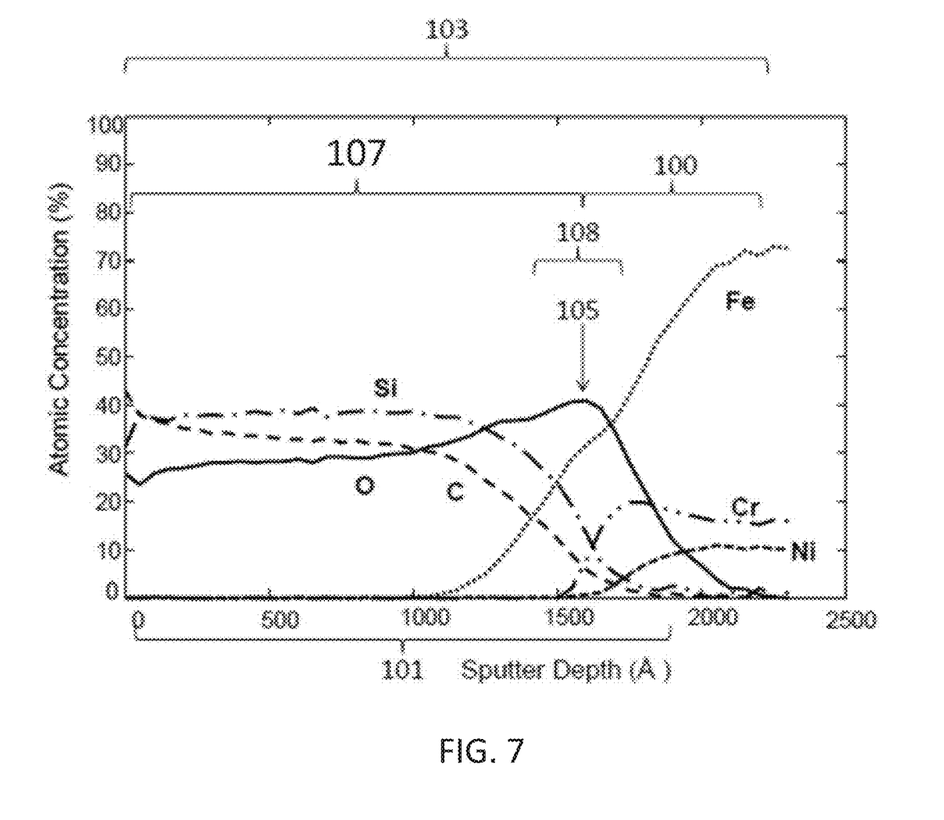
FIG. 7 shows an Auger Electron Spectroscopy plot of an article having a layer formed from decomposition of material followed by oxidation with water according to an embodiment of the disclosure.

In one embodiment including the oxidation (step 208) using water as the oxidant, the article 103 includes a composition as is shown in the Auger Electron Spectroscopy plot of FIG. 7 or a similar variation thereof.

The post-oxidation functionalization (step 210) is or includes thermal coupling of one or more materials.

Figure 4:
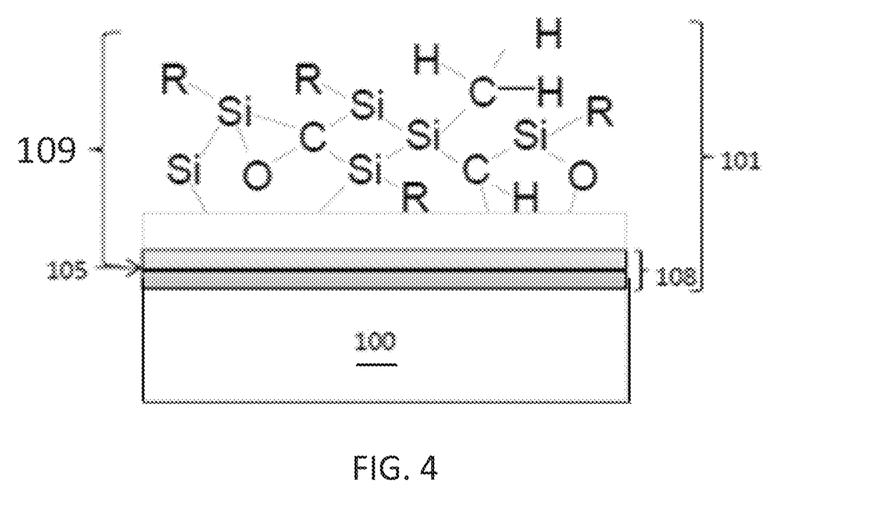
FIG. 4 shows a schematic view of an article having a coating with an oxidized-then-functionalized layer formed according to an embodiment of the disclosure.
Figure 5:
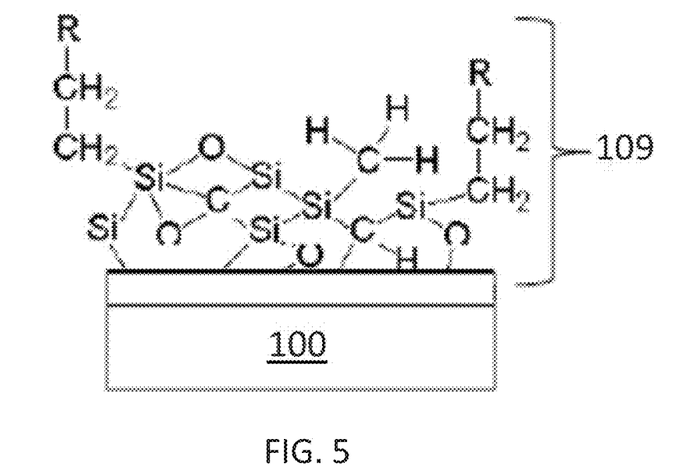
FIG. 5 shows a schematic view of an article having a coating with an oxidized-then-functionalized layer formed according to an embodiment of the disclosure.

In one embodiment, the post-oxidation functionalization (step 210) modifies the oxidized layer 107, for example, by heating and/or modifying the surface, to form the oxidized-then-functionalized layer 109 shown in FIGS. 4-5. Heat, exposure times, diluent gases, and pressures are adjusted to affect the degree of post-oxidation functionalization (step 210). Control of this degree of the post-oxidation functionalization (step 210) imparts predetermined properties. In one embodiment, the oxidized layer is exposed to an organosilane reagent at a temperature of about 300° to 600° C., for about 1 to 24 hours and at a pressure of about 5 to 100 psia, in some cases about 25 psia, about 27 psia, about 54 psia, or any suitable ranges there between. In one embodiment, inert diluent gases are used, such as argon or nitrogen, for example, at partial pressures of about 1 to 100 psia to assist the reaction.

In one embodiment, the oxidized-then-functionalized layer 109 has a contact angle for deionized water on a mirror surface of greater than about 105°, greater than about 110°, greater than about 112°, between about 100° and about 114°, about 110.3°, about 112.1°, about 113.7°, or any suitable range, sub-range, combination, or sub-combination thereof. Additionally or alternatively, in one embodiment, the oxidized-then-functionalized layer 109 has a contact angle for deionized water on a mirror surface that is less than polytetrafluoroethylene, for example, by about 1°, about 2°, between about 1° and about 2°, or any suitable range, sub-range, combination, or sub-combination thereof.

In one embodiment, the oxidized-then-functionalized layer 109 has a contact angle for deionized water on a rough surface of greater than about 140°, greater than about 145°, between about 140° and about 150°, about 142.7°, about 145.7°, about 148.1°, or any suitable range, sub-range, combination, or sub-combination thereof. Additionally or alternatively, in one embodiment, the oxidized-then-functionalized layer 109 has a contact angle for deionized water on a rough surface that is greater than polytetrafluoroethylene, for example, by about 25°, about 30°, between about 20° and about 35°, or any suitable range, sub-range, combination, or sub-combination thereof.

In one embodiment, the oxidized-then-functionalized layer 109 has greater anti-stiction properties than the oxidized layer 107, for example, formed with zero air as the binding reagent. As such, in one embodiment of the coating process 200, the oxidized-then-functionalized layer 109 has increased anti-stiction.

By modifying and varying the R-groups, or by using other molecules capable of hydroxyl reactivity, surface properties of the oxidized-then-functionalized layer 109 are adjusted. For example, in one embodiment, the adjustments increase or decrease hardness and anti-stiction, wear resistance, inertness, electrochemical impedance, contact angle, or a combination thereof, thereby providing physical performance characteristics expanding the applicability and durability for use in biomedical and marine fields.

The following Examples show various elements relating to the disclosure. Properties and parameters disclosed within the Examples should be considered as being disclosed within the Detailed Description of the Invention, whether comparative in nature or illustrative in nature.

Example 1

A first example includes performing the process 200 on a sensor of a Quartz Crystal Microbalance with Dissipation monitoring (QCM-D) system to form the coating 101. QCM-D is employed as a highly sensitive mass sensor to detect mass uptake or release on the $ng/cm^2$ scale at the sensor surface by interpreting changes in the quartz resonance frequency. The coating 101 includes protein-repellant properties formed on the surface of a QCM-D sensor. The QCM-D sensor is a circular quartz crystal of 14 mm in diameter and 0.3 mm in thickness. The quartz crystal is coated with a layer of gold electrode (40-1,000 nm in thickness) on both sides for electrical contact. On one side of the crystal, the gold is further coated with medical-grade 316L stainless steel. The process 200 includes the thermal decomposition (step 204) of the dimethylsilane applying the coating 101 to the QCM-D sensor substrate for 6 to 15 hours at 10 to 30 psia gas at 450° C. to form the layer 102.

The layer 102 is then oxidized (step 208) with zero air for 2 hours at about 1 to 200 psia gas at a temperature between 250-500° C. to form the oxidized layer 107. The process 200 then includes post-oxidation functionalization (step 210) of the oxidized layer 107 by introducing trimethylsilane to an evacuated chamber including the oxidized layer 107 at 400-500° C. and 25 psia and reacted for 5-10 hours to form the coating 101.

Contact angle is measured to be 92.3° on the coated stainless steel surface showing hydrophobic property. The coating thickness is measured to be 250 nm.

Example 2

The second example includes performing the process 200 as described in Example 1 on the exterior and interior surfaces of a medical-grade 316L stainless steel probe, capable of use in an in vitro medical diagnostic system. The probe has an internal diameter in the range of 1 mm to 3 mm. The process 200 forms the coating 101 on the exterior and the interior surfaces of the probe.

Contact angle is measured to be 92.3° on the coated stainless steel surface showing hydrophobic property. The coating thickness is measured to be about 27 nm in the interior surface.

Example 3

The third example includes performing the process 200 as described in Example 1 on a rectangular panel of 316L stainless steel having a size of 4 inches by 8 inches (10.2× 20.3 cm) and 0.6 cm in thickness. Holes having a 1.3 cm diameter are drilled 2 cm from the sides of each corner of the panel. The coating 101 is formed by the process 200 on all surfaces of the panel. The coating 101 is then exposed to biofouling in a seawater environment to ascertain the relative antifouling performance compared to reference surfaces. Results show that the coating 101 includes resistance to biofouling that is greater than coatings failing to include one or more of the features described herein.

Contact angle is measured to be 92.3° on the coated stainless steel surface showing hydrophobic property. The coating thickness is measured to be about 1,000 nm.

While only certain features and embodiments of the invention have been shown and described, many modifications and changes may occur to those skilled in the art (for example, variations in sizes, dimensions, structures, shapes and proportions of the various elements, values of parameters (for example, temperatures, pressures, etc.), mounting arrangements, use of materials, colors, orientations, etc.) without materially departing from the novel teachings and advantages of the subject matter recited in the claims. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation specific decisions may be made. Such a development effort might be complex and time consuming, but would nevertheless be a routine undertaking of design, fabrication, and manufacture for those of ordinary skill having the benefit of this disclosure, without undue experimentation.

What is claimed is:

1. A thermal chemical vapor coated article, comprising:
a coating on the thermal chemical vapor coated article, the coating formed by thermal decomposition, oxidation then functionalization;
wherein the thermal chemical vapor coated article is a medical device requiring resistance to protein adsorption;
wherein the coating is resistant to the protein adsorption and is on a substrate heated during the thermal decomposition.

2. The thermal chemical vapor coated article of claim 1, wherein the thermal decomposition is by introduction of dimethylsilane.

3. The thermal chemical vapor coated article of claim 1, wherein the oxidation is by introduction of zero air.

4. The thermal chemical vapor coated article of claim 1, wherein the functionalization is by introduction of trimethylsilane.

5. The thermal chemical vapor coated article of claim 1, wherein the medical device is a biomedical device, surgical equipment, a portion of a medical diagnostic sampling system, a medical implant, or a combination thereof.

6. The thermal chemical vapor coated article of claim 1, wherein the substrate is stainless steel.

7. The thermal chemical vapor coated article of claim 6, wherein the stainless steel includes 316 stainless steel.

8. The thermal chemical vapor coated article of claim 1, wherein the substrate is titanium.

9. The thermal chemical vapor coated article of claim 1, wherein the substrate is composite metal.

10. The thermal chemical vapor coated article of claim 1, wherein the substrate is glass.

11. The thermal chemical vapor coated article of claim 1, wherein the coating is positioned in a tube, the tube having an internal diameter of between 1 millimeter and 3 millimeters.

12. The thermal chemical vapor coated article of claim 1, wherein the coating is positioned in a tube, the tube having an internal diameter of less than 3 millimeters.

13. The thermal chemical vapor coated article of claim 1, wherein the coating is positioned in a tube, the tube having an internal diameter of between 0.1 millimeter and 1 millimeters.

14. The thermal chemical vapor coated article of claim 1, wherein the coating is positioned in a tube, the tube having an internal diameter of between 0.1 millimeter and 3 millimeters.

15. The thermal chemical vapor coated article of claim 1, wherein the coating has a thickness of between about 100 nm and about 1,000 nm.

16. A thermal chemical vapor coated article, comprising:
a coating on the thermal chemical vapor coated article, the coating formed by thermal decomposition on a stainless steel surface, oxidation then functionalization;
wherein the thermal chemical vapor coated article is a medical device requiring resistance to protein adsorption;
wherein the coating is resistant to the protein adsorption and is on a substrate heated during the thermal decomposition;
wherein the thermal decomposition is by introduction of dimethylsilane;
wherein the oxidation is by introduction of zero air;
wherein the functionalization is by introduction of trimethylsilane; and
wherein the medical device is a biomedical device, surgical equipment, a portion of a medical diagnostic sampling system, a medical implant, or a combination thereof.

17. The thermal chemical vapor coated article of claim 1, wherein the coating is amorphous.

18. The thermal chemical vapor coated article of claim 1, wherein the coating includes an amorphous array of Si-C bonds.

* * * * *